United States Patent
Bracone et al.

(10) Patent No.: US 10,368,542 B2
(45) Date of Patent: *Aug. 6, 2019

(54) METHODS FOR COLLECTING AND PROCESSING AUTOGRAFTS, PROCESSED AUTOGRAFTS, KITS FOR COLLECTING AND TRANSPORTING AUTOGRAFTS, AND TOOLS FOR PREPARING AUTOGRAFTS

(71) Applicant: LifeNet Health, Virginia Beach, VA (US)

(72) Inventors: Roberto Bracone, Hampton, VA (US); Jingsong Chen, Virginia Beach, VA (US); Silvia Chen, Virginia Beach, VA (US); James A. Clagett, Snohomish, WA (US); Marilyn Gatin, Indianapolis, IN (US); Daniel Osborne, Virginia Beach, VA (US)

(73) Assignee: LifeNet Health, Virginia Beach, VA (US)

(*) Notice: Subject to any disclaimer, the term of this patent is extended or adjusted under 35 U.S.C. 154(b) by 302 days.

This patent is subject to a terminal disclaimer.

(21) Appl. No.: 14/031,033

(22) Filed: Sep. 18, 2013

(65) Prior Publication Data
US 2014/0017785 A1    Jan. 16, 2014

Related U.S. Application Data

(63) Continuation of application No. 12/825,033, filed on Jun. 28, 2010, now Pat. No. 8,541,233.

(60) Provisional application No. 61/220,779, filed on Jun. 26, 2009.

(51) Int. Cl.
*A61F 2/46*    (2006.01)
*A61F 2/28*    (2006.01)
*A01N 1/02*    (2006.01)

(52) U.S. Cl.
CPC .......... *A01N 1/0215* (2013.01); *A61F 2/2875* (2013.01); *A61F 2/4644* (2013.01); *A61F 2/28* (2013.01); *A61F 2310/00359* (2013.01)

(58) Field of Classification Search
CPC ........ A01N 1/0215; A61F 2310/00359; A61F 2/28; A61F 2/2875; A61F 2/4644
See application file for complete search history.

(56) References Cited

U.S. PATENT DOCUMENTS

| | | |
|---|---|---|
| 5,333,626 A | 8/1994 | Morse |
| 6,293,970 B1 * | 9/2001 | Wolfinbarger, Jr. .......................... A61F 2/4644 623/16.11 |
| 6,503,279 B1 * | 1/2003 | Webb .................... A61F 2/4465 623/17.16 |
| 8,541,233 B2 * | 9/2013 | Bracone ................ A61F 2/2875 435/366 |
| 2004/0067582 A1 * | 4/2004 | Wolfinbarger, Jr. ...... A01N 1/00 435/366 |
| 2008/0077251 A1 * | 3/2008 | Chen ........................ A01N 1/02 623/23.72 |

OTHER PUBLICATIONS

Linden, J. et al "Professional Standards in Cell and Tissue Processing" Cell Transplantation, 1995, vol. 4, No. 5, pp. 441-446.*
Vangsness, C.T. Jr., "Indepth Look at Allograft Safety: Overview of Allograft Soft Tissue Processing" American Academy of Orthopaedic Surgeons (AAOS) Bulletin, Feb. 2004, 12 pages.*
Vangsness CT Jr., Garcia IA, Mills CR, Kainer MA, Roberts MR, Moore TM. "Allograft transplantation in the knee: tissue regulation, procurement, processing, and sterilization." Am J Sports Med. May-Jun. 2003, 31(3), pp. 474-481.*
Grayson ,et al "Effects of Initial Seeding Density and Fluid Perfusion Rate on Formation of Tissue-Engineered Bone" Tissue Eng Part A. Nov. 2008 ; 14(11): 1809-1820. doi:10.1089/ten.tea.2007.0255 (Year: 2008).*
Zhang J; Peng F; Liu Z; Luan J; Liu X; Fei C; Heng X "Cranioplasty with autogenous bone flaps cryopreserved in povidone iodine: a long-term follow-up study" J Neurosurg. Dec. 2017;127(6):1449-1456. doi: 10.3171/2016.8.JNS16204. Epub Feb. 10, 2017. (Year: 2017).*
Tirakotai W "Cranioplasty Using Frozen and Irradiation Treated Bone Allograft" Thesis: Mahidol University, 2000, pp. 1-20 (ISBN 974-644-834-9) (Year: 2000).*
Zheng MH; Power RA; Openshaw JN; Price RI; Day RE; Winter J; Cowie A; Wood DJ "Effects of Gamma Irradiation on the Mechanical Properties of Human Cortical Allograft Bone" Sterilisation of Tissues Using Ionising Radiations, Woodhead Publishing Series in Biomaterials, 2005, pp. 141-149. (Year: 2005).*
Roux et al. (1996) Development of reconstruction techniques of the anterior skull base after tumor excision, Annales d'oto-laryngologie et de chirurgie cervico faciale: bulletin de la Societe d'oto-laryngologie des hospitaux de Paris, pp. 29-33 (and PubMed English Abstract, 1 page).
Grossman et al. (2007) Deep-freeze preservation of cranial bones for future cranoplasty: nine years experience in Soroka University Medical Center, Cell and Tissue Banking, 8:243-246.
Meijer et al. (2007) Bell-based bone tissue engineering, PLoSMed, 4:260-264.

* cited by examiner

*Primary Examiner* — Aaron J Kosar
(74) *Attorney, Agent, or Firm* — RatnerPrestia

(57) ABSTRACT

The present invention is directed to methods for collecting and processing autografts, processed autografts, kits for collecting and transporting autografts, and tools for preparing autografts. It is also directed to autologous bone grafts, and methods of preparing them.

35 Claims, 1 Drawing Sheet

METHODS FOR COLLECTING AND PROCESSING AUTOGRAFTS, PROCESSED AUTOGRAFTS, KITS FOR COLLECTING AND TRANSPORTING AUTOGRAFTS, AND TOOLS FOR PREPARING AUTOGRAFTS

FIELD OF THE INVENTION

The present invention relates to methods for collecting and processing autografts, processed autografts, kits for collecting and transporting autografts, and tools for preparing autografts. The present invention further relates to autologous bone grafts, and methods of preparing them. The present invention also relates to autologous cranial bone flaps, and methods of preparing them.

BACKGROUND OF THE INVENTION

Approximately 30,000 traumatic brain injuries that require decompressive craniectomy (e.g., removal of a cranial bone flap) occur in the United States every year. Decompressive craniectomies are used to treat patients with massive brain swelling following either trauma or acute cerebral infarction to reduce intracranial pressure. Intracranial subdural grid monitoring is used as a diagnostic technique in patients with intractable partial epilepsy to identify an epileptogenic focus for surgical intervention, which also requires the removal of a bone flap from a patient. In some patients surgical removal of a cranial bone flap is necessary to provide access to a tumor or an aneurysm. Immediately following such surgeries, particularly in decompressive craniectomies, the surgical defect may be left open for some period of time, in order to permit swelling and inflammation of brain tissue to recede. The wound may be temporarily covered by a helmet and/or bandages as the patient recovers.

However at some time after such surgical procedures (i.e., decompressive craniectomy, or intracranial electroencephalography, among others) in which bone is explanted from a patient's skull, it becomes necessary for a surgeon to provide a structural replacement that will act as a protective barrier for the patient's brain in the long term. Several factors are considered by surgeons when selecting a replacement including: (1) tissue reactions including immunogenic responses, metal toxicities reactions, and others, (2) fit, (3) potential for infection, and (4) aesthetic results. Surgeons may store the patient's own cranial bone flap for future re-implantation, or they may choose from several synthetic replacements (i.e., poly-methyl-methacrylate (PMMA) implants, hydroxyapatite implants, or titanium implants, among others) for reconstruction.

Re-implanting the patient's own bone is considered to be the best option by the majority of surgeons. In contrast to synthetic replacements, which may cause immunological reactions or other tissue reactions, an autologous cranial bone flap does not pose this risk as it is the patient's own tissue. While synthetic replacements may require significant manipulation to create a good fit and to produce a good cosmetic effect, an autologous bone flap matches the contour of the patient's defect and provides a more natural appearance after healing. In fact, synthetic implants have a number of disadvantages: (1) their preparation can be difficult, time-consuming, and expensive, (2) clinical and aesthetic outcomes can be unpredictable, (3) they do not permit osteointegration, (4) resorption of host bone may occur at the implant site requiring additional reconstructive surgery, and (5) immunogenic responses to the synthetic materials are a possibility. The problems associated with synthetic implants are increased, when the defect being repaired is relatively large. Despite their drawbacks, many hospitals still choose synthetic implants, because (1) they do not have the facilities to safely store/process bone flaps, or (2) they view the use of synthetic implants as less likely to result in an infection at the surgical defect. The rate of infection at a surgical defect closed with a patient's re-implanted bone flap can be relatively high (estimates have been placed between 2% and 20%).

Surgeons have tried a variety of methods to minimize the risk of infection associated with the use of autologous bone flaps to close defects, including: ethylene oxide and/or steam sterilization, freezing, boiling in saline, immersion in hydrogen peroxide solution, and storage in the patient by surgical intra-abdominal placement. These methods have met with only limited success. Still further, many surgical facilities do not have access to resources that would permit them to implement methods of treating bone flaps (for example, many facilities do not have freezers dedicated to autograft tissue storage). Also, some of the methods create additional problems or potential liability for the surgical facilities (for example, if tissue freezers are available, they must be properly overseen and maintained to prevent cross-contamination of stored tissues and unintended thawing of the freezer contents; or if intra-abdominal placement is used for storage of a bone flap, the additional surgery may increase the likelihood of surgical complications in the patient).

When an autologous bone flap does become contaminated by an infection, the surgeon is often forced to remove and discard it, and to fashion a synthetic replacement. Alternatively, the surgeon may treat the contaminated bone flap with steam sterilization or in situ antibiotic irrigation. Neither is an ideal solution. For example, in situ antibiotic irrigation involves removing the contaminated bone flap, scrubbing it with povidone-iodine solution, and soaking in a hydrogen peroxide solution, while the wound is debrided. The bone flap is then re-implanted and an irrigation system is installed with it, and antibiotic medications are infused through the system for several days. The in situ antibiotic irrigation requires a complex set-up and treatment regimen, and an extended hospital stay. It is also ineffective in some situations (i.e., where there is sinus involvement, or when the defect is at the skull base, among others), and it has the potential for causing undesirable immunogenic reactions.

Using methods and autografts of the present invention, hospitals may be provided with autologous grafts that are less expensive than synthetic implants, aesthetically and clinically satisfactory, well-fitting and easy to use, and safe.

SUMMARY OF THE INVENTION

The present invention provides methods for collecting and processing autografts (e.g., autologous tissue grafts), autografts, kits for procuring and transporting autografts, and tools for preparing autografts.

The method of the present invention may comprise a method for collecting and processing autologous tissue for re-implantation in a patient comprising surgically removing a piece of tissue from a patient; treating the tissue with one or more treatment solutions; processing the treated tissue; and re-implanting the processed tissue into the patient. The method of the present invention may also consist of surgically removing a piece of tissue from a patient; treating the tissue with one or more treatment solutions; processing the treated tissue; and re-implanting the processed tissue into the patient.

Certain aspects of the present invention are directed to methods for collecting and processing autologous tissue for re-implantation in a patient. Some methods of the present invention may include: (1) surgically removing a piece of a tissue from a patient to obtain a collected tissue; (2) pre-treating the collected tissue with at least one treatment composition to produce a pre-treated tissue; (3) shipping the pre-treated tissue to a tissue processing facility; (4) processing the pre-treated tissue to produce a processed tissue; (5) shipping the processed tissue to a surgical facility; and (6) re-implanting the processed tissue into the patient from whom the piece of tissue was surgically collected. Other methods of the present invention may consist essentially of (1) surgically removing a piece of a tissue from a patient to obtain a collected tissue; (2) pre-treating the collected tissue with at least one treatment composition to produce a pre-treated tissue; (3) shipping the pre-treated tissue to a tissue processing facility; (4) processing the pre-treated tissue to produce a processed tissue; (5) shipping the processed tissue to a surgical facility; and (6) re-implanting the processed tissue into the patient from whom the piece of tissue was surgically collected.

In some aspects of the invention, the tissue may be removed from a subject. The subject may be a patient. The patient may be an animal. The animal may be a mammal. The mammal may be a human, a cow, a pig, a goat, a dog, a horse, or a sheep.

In some aspects of the present invention, a tissue collected and processed using methods of the present invention may include cartilage, bone, or soft tissue (i.e., tendons, among others). Certain aspects of the present invention are directed to methods for collecting and processing autologous bone tissue for re-implantation in a patient, and in some methods of the present invention, the autologous bone that is collected and processed is autologous cranial bone such as a cranial bone flap. For example, a craniectomy is performed to remove the cranial bone flap. The bone flap may be processed for re-implantation such as in a future cranioplasty. A collected tissue may be contaminated with at least one of debris, a bacterium, a single-celled eukaryote (i.e., a fungus or amoeba, among others) or a virus.

Besides cranial bone flaps, other types of tissues including but not limited to facial bone, tibial bone, femoral bone, bones of the extremities, periprosthetic bone, ligaments, tendons, and muscle, among others, may be removed from a patient, processed, treated, and re-implanted. Facial bones may include the mandible, frontal bone, parietal bone, sphenoid bone, temporal bone, nasal bone, among others. Bones of the extremities may include bones of the hands, feet, arms, and others. Periprosthetic fractures may be difficult to fix. The present process provides a method of cleaning the bone with the implant attached to it as a way of fixing periprosthetic.

A surgeon would prefer to re-implant the tissue into a patient, rather than replace it with an allograft or synthetic graft. However, existing methods for preparing such tissues for re-implantation may present an unacceptable level of risk for post-operative infection. For example, tissues such as bones may be damaged due to trauma, infection, or disease (i.e., cancer, among others), and a surgeon may wish to re-implant the facial bone, but might be unwilling to do so knowing the possible risks of infection using known methods. Depending on the nature of a facial trauma there may be dirt or debris in the wound, and these need to be removed to reduce the likelihood of infection before damaged facial bone can be re-implanted. In some cases, a soft tissue (i.e., ligament, tendon, muscle or fascia, among others) may be infected or be unclean due to trauma, and a surgeon may need to remove the tissue. The surgeon might prefer to re-implant the soft tissue, but be unable to do so using existing methods without a serious risk of infection. Similarly, a surgeon may need to remove some bone, when a patient presents with a periprosthetic fracture (i.e., a fracture of a bone surrounding a knee or hip replacement, among others), and the surgeon may wish to re-implant the bone (which may be attached to part of a prosthesis), but current methods of preparing the removed bone may not be sufficiently rigorous for a surgeon to accept this as a safe alternative.

In some aspects of the present invention, a collected tissue is treated with at least one treatment composition before being shipped to a tissue processing facility. In certain aspects of the present invention, a method for collecting and processing an autologous tissue may include at least one cleaning step and at least one rinsing step. In some aspects of the present invention, a collected tissue is processed using Allowash® treatment (a proprietary tissue cleansing process of LifeNet Health, Virginia Beach, Va.) at a tissue processing facility.

The tissue may be sterilized by irradiation. The tissue may be irradiated with gamma rays. Other methods of sterilizing the tissue include but are not limited to using supercritical carbon dioxide, electron beam, and ethylene dioxide. The tissue may be sterilized prior to or after processing. The tissue may be sterilized prior to packaging or after being packaged for shipment.

The tissue processing facility may be the surgical facility where the tissue is removed and/or re-implanted or a separate surgical facility. The tissue processing facility also may be a facility separate from the surgical facility.

The tissue may be packaged for shipment to the processing facility for processing. After processing, the tissue may be packaged for shipment to the surgical facility for re-implantation. Prior to or after packaging, the processed tissue may be irradiated for sterilization purposes before shipment to the proper facility.

In one aspect of the invention, during pre-treatment or after pre-treatment of the tissue, one or more bactericidal agent and/or one or more preservation agent or plasticizer may be added to the tissue prior to processing or shipment to a processing facility for processing. In another aspect of the invention, during processing or after processing of the tissue, one or more bactericidal agent and/or one or more preservation agent or plasticizer may be added to the tissue for storage and/or shipment to a surgical facility for re-implantation.

In certain aspects of the present invention, an instrument insertion site is added to a collected tissue for ease in maneuvering the tissue. In some aspects of the present invention, at least one of a composition including an allograft tissue, a composition including a synthetic graft material, or a biocompatible adhesive is added to an autograft (autologous tissue) during processing. In certain aspects of the present invention, a processed tissue that has been packaged is gamma irradiated before re-implantation. In some aspects of the present invention a packaged processed tissue has a sterility assurance level (SAL) of at least about $10^{-6}$. In certain aspects of the present invention, a processed tissue is stored for between about 3 days to 5 days, 3 days and 1 year before it is re-implanted in the patient. In some instances, the tissue is processed and stored at the surgical facility or the hospital and re-implanted. As an example, for brain tumor patients or for injuries resulting from battle field trauma, the processed tissues may be re-implanted in the patient in about 3 to 5 days and therefore will not be shipped or stored at a tissue processing facility but will be processed, treated, and stored at the surgical facility or hospital and re-implanted.

In some methods of the present invention, a status report regarding an autologous tissue is entered into a computer accessible information system at each step in the method. In certain methods of the present invention, a tracking device is kept with a tissue throughout the method.

Some aspects of the present invention are directed to autologous tissue procurement kits for use in collecting a piece of a tissue from a patient. In certain aspects of the present invention, the kit may include (1) an instruction sheet containing at least a contact phone number for a tissue processing facility, a description of autologous tissue collection kit use, and a description of a method of packaging a collected tissue; (2) at least one label including a space for a patient's identifying information to be entered; (3) a sealable tissue container; (4) a shipping container; and (5) at least one of a treatment composition, and (6) an electronic storage device (e.g., a microchip) for storing information electronically. Some kits of the present invention may include a tool for creating an instrument insertion site in a tissue, or a surgical instrument for re-implanting an autograft having an instrument insertion site.

As an example, a kit of the present invention may include (1) a container for holding the tissue after removal from patient at the surgical facility; (2) a treatment solution for cleaning and/or disinfecting the tissue at the surgical facility; (3) temporary storage and shipment solution; (4) a device for adding an instrument insertion site to the tissue for ease of maneuvering the tissue; (5) a microchip for tracking the tissue; (6) a container for storage at the surgical facility and/or shipment to the processing facility; and (7) a cooler comprising a compartment for storing the tissue and other compartments for storing other accessories. The kit may include more than one of each of these components. The present invention also provides methods for using the kit disclosed herein for procuring and processing autologous tissues for re-implantation in a patient.

Certain aspects of the present invention are directed to autologous bone grafts for re-implantation into the patient. The re-implanted bone graft may include a piece of bone that is autologous to the recipient, and the piece of bone may include an instrument insertion site that is capable of securely coupling to a surgical placement instrument and to at least one of (1) a solution injector and (2) a solution evacuator. In some aspects of the present invention, the autologous bone graft further includes at least one of an allograft tissue and a synthetic implant material. In certain aspects of the present invention, the autologous bone graft is sterile. Some autologous bone grafts of the present invention may be prepared from a tissue that had been contaminated with a bacteria or a virus. Certain aspects of the present invention are directed to packaged autologous bone grafts including a package containing an autologous bone graft having a sterility assurance level of at least about $10^{-6}$.

The method of the present invention also may be performed with organs surgically removed from a subject or a patient. As an example, the organ may be surgically removed from a subject, pretreated before processing, processed, and re-implanted into the subject. The organ may be packaged for shipping to a processing facility. The processed organ may be stored after processing. The processed organ may be packaged and shipped to a surgical facility for re-implantation.

BRIEF DESCRIPTION OF THE DRAWINGS

FIG. 1A is a picture of the bone flap of Example 1 before processing.

FIG. 2A is a picture of the bone flap of Example 2 before processing.

FIG. 3A is a picture of the bone flap of Example 3 before processing.

DESCRIPTION OF THE INVENTION

Figure 1A:
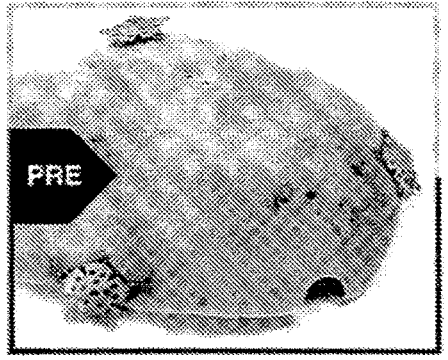
FIGS. 1A and B.

Some aspects of the present invention are directed to methods for surgically removing a tissue from a patient to obtain a tissue, pre-treating the tissue prior to processing, and processing the tissue for re-implantation in a patient.

Certain methods of the present invention may include the steps of: (1) surgically removing and collecting a piece of a tissue from a patient to produce a collected tissue; (2) treating (or pre-treating) the tissue at a surgical facility prior to processing at a tissue processing facility; (3) shipping the collected tissue to a tissue processing facility; (4) processing the collected tissue to produce a processed tissue; (5) shipping the processed tissue to a surgical facility; and (6) re-implanting the processed tissue into the patient from whom the piece of tissue was surgically collected.

In some instances, the surgically removed tissue may need to be re-implanted a few days after surgical removal from the patient. The tissue may be processed and stored at the surgical facility for re-implantation in a few days, for example 3 to 5 days, after surgical removal. Accordingly, the tissue processing and storage facility may be the surgical facility or hospital. Thus, certain methods of the present invention may include the steps of: (1) surgically removing and collecting a piece of a tissue from a patient to produce a collected tissue; (2) treating (or pre-treating) the collected tissue at a surgical facility; (3) processing the collected tissue at the surgical facility; and (4) re-implanting the processed tissue into the patient from whom the piece of tissue was surgically collected. A collected tissue processed at a surgical facility may optionally be stored at a surgical facility or at an external storage facility before being re-implanted, in some aspects of the present invention. In certain methods of the present invention, a collected tissue processed at a surgical facility may be re-implanted in the patient within about 3 days to about 5 days (i.e., where tissue is removed to access a brain tumor or during surgical intervention of a battlefield trauma).

In some methods of the present invention, the collected and processed tissue includes at least one of cartilage, bone, and a soft tissue from the patient. The tissue includes bone from the patient, in some aspects of the present invention. In certain aspects, the bone includes cranial bone, facial bone, tibial bone, femoral bone, bone from the extremities (i.e., the hands, feet, and arms), and bone from a periprosthetic fracture. The bone tissue includes cranial bone from the patient in certain aspects. In some aspects, the bone tissue includes a cranial bone flap from the patient. Soft tissue may include but are not limited to tendon, ligament, fascia, and muscle. In certain aspects of the present invention, the tissue collected and processed includes (1) bone and soft tissue (i.e., tendon) from the patient, or (2) bone and articular cartilage from the patient. A tissue that is collected from the patient for processing may be contaminated with at least one of debris, a bacterium, a single-celled eukaryote (i.e., a fungus, among others) and a virus. Accordingly, the tissue may need to be treated and processed prior to re-implantation in the patient.

In certain aspects of the present invention, a method of collecting and processing autologous tissue includes providing a tissue collection kit that is used in the surgical removal of tissue from the patient. In some aspects, the tissue may be a cranial bone flap that has been surgically removed during a decompressive craniectomy, an intracranial electroencephalography procedure, a brain tumor surgery, or a brain aneurysm surgery, among others. In certain methods of the present invention, a cranial bone flap may be collected from the patient during a decompressive craniectomy, or after infection of a part of the patient's skull.

In some aspects of the present invention, a tissue that has been collected from the patient may be pre-treated with one or more treatment compositions before it is packaged and shipped to a tissue processing facility for processing. The treatment composition may be antimicrobial solution, an antibiotic solution, a plasticizer solution, sterile water, sterile saline, or a detergent solution, among others. The treatment solution may also comprise the proprietary Allowash® solution technology of LifeNet Health, Virginia Beach, Va. The plasticizer solution may contain glycerol. The treatment composition may also include a disinfectant and/or a plasticizer. In some aspects, a treatment composition may include hydrogen peroxide. In certain aspects, a treatment composition may include a plasticizer, such as glycerol. In other embodiments, the treatment may comprise the use of a bactericidal and/or a virucidal agent. In certain aspects of the present invention, a treatment composition may include antibiotic, plasticizer, water, a buffer, a detergent, an enzyme, a bioactive factor, or a combination thereof. A treatment composition may be a treatment solution, in certain aspects of the present invention. In some aspects of the present invention, a treatment composition may reduce the bioburden of a collected tissue. A collected tissue may be placed in a treatment container with a treatment and/or short term or temporary storage composition before it is shipped to a processing facility in certain aspects of the present invention. The short term or temporary storage composition may include hydrogen peroxide and/or a plasticizer in some aspects of the present invention.

During pre-treatment or after pre-treatment of the tissue, one or more bactericidal agent and/or one or more preservation agent or plasticizer may be added to the tissue prior to processing or prior to shipping to a processing facility for processing. Moreover, during processing or after processing of the tissue, one or more bactericidal agent and/or one or more preservation agent or plasticizer may be added to the tissue for storage and/or shipment to a surgical facility for re-implantation.

The present invention also provides a container for holding the tissue. The container may have one or more openings or ports for liquids to enter and exit the container and an opening for placing the tissue into the container. The container may be deformable, nondeformable, or a combination thereof in which the container has a nondeformable exterior and a deformable interior. The container may be made of material that enables it to be deformable, or nondeformable or a combination thereof. The container may have an inlet opening and an outlet opening for rinsing solutions, treatment solutions, and storage solutions to enter and exit. The opening on the container for placing the tissue into the container or for removing the tissue from the container may be closed with a zipper or with a clamp. The process of cleaning, disinfecting, treating, storing, and/or shipping of the tissue may all be performed in the container of the present invention. The container may be a bag or may contain a bag with the features described above for the container.

In some aspects of the present invention, a collected tissue is packaged by a method including placing it into a shipping container with a tracking device and/or labeling the shipping container with at least a patient identification number. In certain methods of the present invention, a collected tissue is packaged by a method including, placing the collected tissue in a container and sealing the container, placing the sealed container into a shipping container, and adding dry ice or wet ice between the sealed container and the shipping container. In some aspects, the shipping container includes an insulating insert. In certain aspects, the shipping container includes a cooler, and in some aspects the cooler includes a temperature regulating device (i.e., a refrigeration unit). A collected tissue may be shipped to a tissue processing facility at room temperature, on dry ice, or on wet ice, in certain methods of the present invention.

In certain aspects of the present invention, a tissue is surgically removed from the patient, packaged, and shipped to a tissue processing facility, where it is unpacked and undergoes processing. In some methods of the present invention, processing (e.g., at the tissue processing facility or the surgical facility) may include at least one of debridement, decontamination, and removal of cellular elements, among others. In some aspects of the present invention, processing causes a tissue to have a reduced bioburden. In certain aspects, processing may include the use of at least one of a detergent, an antimicrobial, an antibacterial, an antibiotic, and an alcohol to affect removal of associated tissues (such as, as bone marrow, lipids, and cellular elements in a bone tissue, among others) and/or contaminants (such as, bacteria and viruses, among others). In some aspects of the present invention, a tissue obtained from a patient may be processed with a solution for removing lipids and blood cells from the tissue such as acetone, with a solution inducing osmotic shock for removing nucleic acids from the tissue, and/or with an oxidizing agent, such as hydrogen peroxide for removing and/or inactivating immunogenic structures and microorganisms. The tissue may also be processed by treating with organic solvents.

In some aspects, processing includes cleaning the tissue. The tissue that was removed from the patient may be cleaned using methods and devices known in the art. In certain aspects of the present invention, a tissue obtained from the patient may be processed using proprietary Allowash® technology of LifeNet Health, Virginia Beach, Va. Processing that involves the use of Allowash® may or may not include debridement. If debridement and Allowash®, or other processing techniques, are used with one another, the debridement may occur either before or after the tissue is processed with the Allowash® or processing solutions. Exemplary methods, compositions, and devices for processing include those disclosed in U.S. Pat. Nos. 6,942,961; 6,482,584; 6,024,735; 5,977,432; 5,977,034; 5,976,104; 5,846,484; 5,820,581; 5,797,871; 5,556,379; 7648676 and 7585461; U.S. Publication Nos. 2008/0188939; 2005/0100862; 2005/0096742; and 2004/0037735; and International Publication No. WO 2004/075935, which are hereby incorporated by reference in their entirety.

In some aspects of the present invention, the processing, at a processing facility or a surgical facility, includes at least one cleaning step and at least one rinsing step. A rinsing step may permit the removal of any residual processing components that may cause a negative tissue reaction in the patient.

Processing may include decellularization or devitalization of a tissue, as is known in the art, in certain aspects of the present invention. Exemplary decellularization and devitalization methods include those disclosed in U.S. Pat. Nos. 7,338,757; 6,743,574; and 6,734,018, among others. Several autografts may be processed by one method at the same time, in some methods of the present invention. In certain aspects of the present invention, processing may include using, for example, centrifugation, sonication, application of a vacuum, or a combination thereof.

In certain methods of the present invention, bone tissue collected from the patient may be demineralized as part of its processing at a tissue processing facility. In some aspects, the bone tissue may be demineralized by exposure to dilute hydrochloric acid, as is known in the art. Any demineralization processes known in the art, may be used to prepare demineralized bone for re-implantation into the patient. Exemplary demineralization processes are described in U.S. Pat. Nos. 6,830,763; 6,534,095; 6,305,379; 6,189,537; 5,531,791; and 5,275,954, which are hereby incorporated by reference in their entirety. In certain methods of the present invention, processing of a bone tissue may include a perforation method. In some aspects of the present invention, processing at a tissue processing facility yields a cleaned, demineralized cranial bone flap or a cleaned, perforated cranial bone flap.

In some aspects of the present invention, processing, at a processing facility or a surgical facility, may include treating the tissue with a solution including glycerol (i.e., proprietary Preservon® treatments of LifeNet Health, Virginia Beach, Va.). In certain aspects of the present invention, tissues collected from the patient may be processed as described in U.S. Pat. Nos. 7,063,726; 6,569,200; 6,544,289; and 6,293,970, which are hereby incorporated by reference in their entirety.

In certain aspects of the present invention, processing may include adding an instrument insertion site in a tissue collected from the patient. An instrument insertion site may be used to connect a syringe or a pump (i.e., a vacuum pump, among others) to a tissue in some aspects of the present invention. Thus, a processing/treatment solution or a rinsing solution may be applied to a tissue by flushing it through the instrument insertion site, in certain aspects of the present invention. Rinsing of an autograft may be done in a surgical facility by coupling a syringe of or a pump for rinsing solution to an instrument insertion site in the autograft and flushing the autograft, in some aspects of the present invention. In certain aspects of the present invention, a processed tissue may be packaged in a syringe-adapted container, and a syringe of rinsing solution may be coupled to the syringe-adapter in a surgery facility where it is rinsed. Alternatively, in some aspects of the present invention, a processing/treatment solution, a storage solution, or a rinsing solution may be drawn through an autograft by methods employing a syringe or a pump (e.g., vacuum) coupled to the instrument insertion site of the autograft.

In some aspects of the present invention, processing, at a processing facility or a surgical facility, may include adding bioactive factors to the tissue that was collected from the patient. Bioactive factors are factors that regulate growth, proliferation, differentiation, migration, and maturation of cells. In some aspects of the present invention, bioactive factors may be osteoinductive factors, chondrogenic factors, cytokines, mitogenic factors, chemotactic factors, transforming growth factors (TGFs), fibroblast growth factors (FGFs), angiogenic factors, insulin-like growth factors (IGFs), platelet-derived growth factors (PDGFs), epidermal growth factors (EGFs), vascular endothelial growth factors (VEGFs), nerve growth factor (NGFs), neurotrophins, bone morphogenetic proteins (BMPs), osteogenin, osteopontin, osteocalcin, cementum attachment protein, erythropoietin, thrombopoietin, tumor necrosis factor (TNF), interferon, colony stimulating factors (CSFs), or interleukins, among others. The bioactive factor may be rhBMP2 (recombinant human BMP2), rhBMP4 (recombinant human BMP4), rhBMP7 (recombinant human BMP7), or rhPDGF (recombinant human platelet-derived growth factor), among others, in some aspects of the present invention. In certain aspects of the present invention, a bioactive factor may be an enzymatically treated or modified bioactive factor. For example, the bioactive factor may have been treated with an enzyme to have a modified activity or treated chemically to have a modified activity.

In certain aspects of the present invention, processing, at a processing facility or a surgical facility, may include applying a composition including at least one of an allograft tissue and a synthetic graft material to the autologous tissue to aid in wound healing, when it is re-implanted in the patient. In some aspects of the present invention, a paste, a gel, a putty, or a sponge may be applied to a surface and/or edge of a processed autologous tissue to improve healing and union, when the tissue is re-implanted in the patient. In certain aspects of the present invention, when the autograft is a cranial bone flap, a sponge (i.e., a collagen sponge) may be applied to cover the bone flap to aid in reconstruction of the patient's periosteum and to improve the remodeling rate of the bone flap. Sponges, gels, pastes, and putties used in some aspects of the present invention may include an allograft material or a synthetic graft material (i.e., polymers, calcium phosphate or hydroxyapatite, among others). For example, sponges and putties including demineralized allograft bone may be used in some aspects of the present invention.

In some methods of the present invention, after an autograft is processed, it is packaged before it is re-implanted in the patient. In certain aspects of the present invention, a packaged processed tissue is gamma irradiated before shipping to the surgical facility. Irradiation of a packaged processed tissue may be performed at the facility where a tissue is processed or at a separate facility. In some aspects of the present invention, a packaged processed tissue is subjected to gamma irradiation (i.e., about 18 kGy to about 58 kGy minimum absorbed dose) at a low temperature (i.e., $-20°$ C. to $-50°$ C.). In certain aspects of the present invention, the gamma irradiation process may be validated not to damage biological or structural capabilities of a tissue graft. In some aspects, a packaged processed tissue of the present invention has a sterility assurance level (SAL) of at least about $10^{-6}$.

After processing, the tissue may be sterilized by irradiation with about 18 KGy to about 25 KGy. It may be necessary to irradiate at a low dosage so as not to compromise the biomechanical properties of the tissue. The tissue may be sterilized with gamma irradiation. In some aspects of the present invention, a tissue obtained from a patient may be sterilized using electron beam, supercritical $CO_2$, or ethylene oxide methods, among others.

In other embodiments of the present invention, the processed tissue may be packaged in a storage solution. The processed tissue may be stored in the storage solution either before or after it is sterilized, for example through gamma irradiation. In certain aspects of the invention, the processed tissue is stored in a storage solution and subsequently sterilized in the storage solution. Examples of storage solutions include, but are not limited to, solutions including glycerol (i.e., proprietary Preservon® treatments of LifeNet Health, Virginia Beach, Va.), or other polyol, high concentration salt solution, for example, sodium chloride, as disclosed in U.S. Pat. No. 6,739,112 (incorporated by reference), and DMSO, as disclosed in U.S. Pat. No. 6,946,098 (incorporated by reference) or combinations thereof.

In some methods of the present invention, packaging of a processed tissue includes placing the processed tissue into a syringe-adapted container. The syringe-adapted container may then be placed into a shipping container, in certain methods. In some aspects of the present invention, a shipping container may include a compartment for holding a container containing a processed tissue and a compartment for holding a graft instruction sheet, and a shipping container may, optionally, include additional compartments. In certain aspects of the present invention, at least one of (1) a microchip, (2) a surgical placement instrument, (3) a biocompatible adhesive (i.e., a fibrin-based adhesive or collagen gel, among others), (4) a composition including synthetic graft materials (i.e., polymers, hydroxyapatite, or calcium phosphate among others) for aiding in wound healing and union, and (5) a composition including an allograft tissue (i.e., collagen, cells, and demineralized bone, among others) for aiding in wound healing and union may also be placed into a shipping container before a packaged processed autologous tissue is shipped to a surgical facility. In certain aspects, the shipping container includes a cooler, and in some aspects the cooler includes a temperature regulating device (i.e., a refrigeration unit).

In some methods of the present invention, a swab culture may be prepared from at least one of the collected tissue, the pre-treated tissue, and the processed tissue. A tissue is swabbed using methods known in the art, and the swab is placed in contact with at least one culture medium under various culture conditions, so that any bacteria, fungi, or other single-celled organisms present may grow, be detected, and be identified. Swab cultures may be prepared using thioglycolate and/or trypticase soy broth media, among others, in certain aspects of the present invention. Swab cultures may be grown at two or more temperatures, and for up to about 14 days, in some methods of the present invention. When a tissue is swab tested before processing, the swab culture may be performed by a surgical facility where the tissue is collected from the patient and/or at a tissue processing facility. Swab cultures may permit a processing facility to monitor the effectiveness of its processing. A swab culture test of a processed tissue may yield no microbial growth (i.e., bacterial growth) in some aspects of the present invention. In certain aspects, a swab culture of a processed tissue may yield no microbial growth, even where the tissue was contaminated before processing.

In certain methods of the present invention, a processed tissue is subjected to a quality assurance review at the tissue processing facility before it is shipped to a surgical facility. Those responsible for quality assurance may release an autologous tissue only after reviewing records to ensure all standards were met during processing, in some aspects of the present invention. In certain aspects of the present invention, a donor records coordinator may ensure final documentation is complete before a processed tissue is sent to a surgical facility to be re-implanted in the patient from which it was originally collected. In some methods of the present invention, a packaged processed autograft is shipped to a surgical facility in an organic, non-toxic and fully biodegradable shipping container with a prepaid return label, and instructions for use. The shipping container may contain at least one of a gel, a putty, a paste, a sponge, and a biocompatible adhesive that can be employed at the defect site during re-implantation of the autograft, so that it may aid in at least one of wound healing, union of the graft with tissue at the implant site, and keeping the graft in place until union of the tissues occurs.

In certain aspects of the present invention, a method of collecting and processing autologous tissue, including surgical collection, and optionally, shipping to and processing at a tissue processing facility, and shipping of the processed tissue to a surgical facility, requires less than two weeks. In some methods of the present invention a processed tissue is stored at a tissue processing facility, a surgical facility, or an independent tissue storage facility for between about 3 days and 1 year before it is re-implanted. When a cranial bone flap is removed from a patient with a traumatic brain injury (TBI), it can take more than six months before that patient is in a condition to have the bone flap re-implanted. Thus, it may be necessary to store a bone graft for some time before it is re-implanted in the patient. In some cases a cranial bone flap created during brain cancer and aneurysm surgery may be re-implanted in the patient in as little as 3 to 4 days. In some aspects of the present invention, storage of a processed tissue occurs in a facility that may be validated annually, have restricted access, have 24-hour monitoring, have internal and/or external alarms, and have a natural disaster recovery program. In certain aspects of the present invention, a processed tissue may be stored in a freezer, and the freezer may be calibrated annually. In some aspects of the present invention, a processed tissue may be stored at a temperature between about −40° C. and about −80° C., or between about −20° C. and about −40° C.

In certain methods of the present invention, a tissue that has undergone processing may be seeded with a plurality of viable cells before it is re-implanted into the patient from whom the tissue was originally collected. In some methods of the present invention, the cells seeded onto the tissue may be allogenic or autogenic to the patient that the tissue will be re-implanted into. Cells may be added to a processed tissue using methods known in the art, in some aspects of the present invention. A tissue collected from a patient that has been processed (as discussed above) may have cultured cells derived from the patient or another individual of the same species added to it before it is re-implanted in the patient, in certain aspects of the present invention. In some aspects of the present invention, bone tissue (i.e., a cranial bone flap) taken from a patient, and then processed, may have cultured osteoblasts derived from the same patient or another individual of the same species added to it before it is re-implanted in the patient. In some aspects of the present invention processed bone tissue to which cells are added may have been demineralized during processing. Methods for adding cells to a demineralized bone tissue known in the art may be use, and exemplary methods are disclosed in U.S. Pat. No. 7,494,811, among others. In certain aspects of the present invention, at least one of osteoblasts, pre-osteoblasts, osteocytes, chondrocytes, chondroblast, periosteal cells, myoblasts, endothelial cells, mesenchymal cells, and fibroblasts may be added to a processed tissue before it is re-implanted in the patient. In some aspects of the present invention the osteoblasts, pre-osteoblasts, chondrocytes, chondroblasts, periosteal cells, myoblasts, endothelial cells, mesenchymal cells, or fibroblasts are cultured from cells derived from a donor or from the same patient receiving the processed tissue autograft.

In some methods of the present invention, a status report is entered into a computer accessible information system at each step (i.e., shipping step, processing step, among others) in the method. In certain methods of the present invention a tracking device is kept near (i.e., within 5 feet) the tissue throughout the method. In some aspects of the present invention, the tracking device includes a microchip. The tracking device may be embedded in the tissue in the form of a microchip. In certain aspects of the present invention, the tracking device includes a thumb drive. The tracking device has at least a patient identification number stored on it, in some aspects of the present invention. In certain aspects of the present invention, processing conditions used with an autologous tissue graft may be stored on the tracking system. Where the tracking system includes a microchip, the microchip may be scanned and information updated at each step in certain methods of the present invention. In some aspects of the present invention, information stored on the microchip is uploaded to an information system that is accessible by at least one of the patient, a representative of the patient, a doctor, a surgical facility, an independent tissue storage facility, and a tissue processing facility.

In certain methods of the present invention, a packaged processed tissue (autograft) may be stored at the surgical facility for some period of time before it is re-implanted in the patient from which the tissue was collected. In some methods, when the autograft is to be stored for a long term it may be stored at between about −40° C. and about −86° C., or for a short term (e.g., less than 6 months) at between about −20° C. and −40° C. Depending on the processed tissue, it may be stored at room temperature. For example, a plasticizer may be added to the tissue during or after the processing step which may allow the processed tissue to be stored at room temperature.

In certain aspects of the present invention, processing may include treating the tissue with a plasticizer (i.e., glycerol, among others). Plasticizers may be added to the solution for temporary storage during or immediately after treatment of the tissue, but prior to packaging the tissue for shipping, in some aspects of the present invention. Plasticizers may also be employed during or after processing of the tissue for storage of the tissue prior to re-implantation. Plasticizers may be employed at concentrations in the range of from about 10% to 100% by weight or volume. Depending on the tissue or organ being plasticized, the present plasticizers may be employed at concentrations in the range of from about 13% v/v to about 100% v/v, from about 50% v/v to about 100% v/v, from about 60% v/v to about 100% v/v, from about 75% v/v to about 100% v/v, from about 10% v/v to about 25% v/v, from about 10% v/v to about 20% v/v, from about 75% v/v to about 90% v/v, from about 75% v/v to about 85% v/v, from about 80% v/v to about 85% v/v, or from about 75% v/v to about 85% v/v of the total volume. As an example, the concentration of plasticizer used to plasticize bone may be greater than about 70% v/v, greater than about 75% v/v, from about 70% to about 90% v/v, from about 75% to about 80% v/v, about 70% v/v, or about 77% v/v.

In certain aspects of the present invention, during processing or at the time a processed autograft is re-implanted, a gel, a paste, a putty, or a sponge that may aid in healing and union, may be applied to a surface and/or an edge of the graft or at the edges of a surgical implantation site. Such gels, pastes, putties, and sponges may contain allograft materials (i.e., demineralized bone powder, and collagen, among others) and/or synthetic materials (i.e., polymers, calcium phosphate, hydroxyapatite, among others). Exemplary gels, pastes, and putties that may be employed in certain aspects of the present invention are sold under the trade names of Grafton® (Osteotech, Inc., Eatontown, N.J.), DBX® (Musculoskeletal Transplant Foundation), Plexur™ Biocomposites (Osteotech, Inc., Eatontown, N.J.), BioSet™ (RTI Biologics, Alachua, Fla.), and Optium DBM® (LifeNet Health, Virginia Beach, Va.), among others. Exemplary compositions are also described in U.S. Pat. Nos. 7,019,192; 7,001,430; 6,911,212, 6,458,375; 6,437,018; 6,326,018; 6,030,635; and 5,702,677, among others known in the art. Collagen sponges may also be used with a re-implanted autograft, in certain embodiments. In some aspects of the present invention, a biocompatible adhesive (i.e., fibrin-based adhesives and collagen gels, among others) may be used to help hold an autograft in place upon re-implantation.

Certain aspects of the present invention are directed to an autologous tissue collection kit for use in collecting a tissue from a patient. Some autologous tissue collection kits of the present invention includes, (1) an instruction sheet containing at least a contact phone number for a tissue processing facility, a description of autologous tissue collection kit use, and a description of a method of packaging a collected tissue; (2) at least one label including a space for a patient's identifying information to be entered; (3) a sealable tissue container; (4) a shipping container; and (5) at least one of a treatment composition and an electronic storage device for storing at least a patient identification number. In some aspects of the present invention, the sealable tissue container in an autologous tissue collection kit may be rigid and configured to fit directly into a centrifuge at a tissue processing facility. Some autologous tissue collection kits of the present invention may include sterile materials for packaging a tissue that is collected, and the materials may be drapes or bags, among others. Certain tissue collection kits of the present invention may contain forms to be filled out on-site when a tissue is collected.

As an example, a kit of the present invention may include (1) a container for holding or storing the tissue after removal from patient at the surgical facility; (2) a treatment solution, such as Allowash®, for cleaning and/or disinfecting the tissue at the surgical facility to reduce the bioburden before processing; (3) temporary storage and shipment solution, for example, a solution containing plasticizer (and optionally a decontaminating agent) which enables the tissue to be shipped at room temperature and eliminates the need to freeze the tissue prior to packaging the tissue for shipping; (4) a device for adding an instrument insertion site to the graft for ease of maneuvering the tissue; (5) a microchip for tracking the tissue; (6) a container for storage at the surgical facility and/or shipment to the processing facility; and (7) a cooler comprising a compartment for storing the autologous tissue and other compartments for storing other accessories. The kit may include more than one of each of these components. The present invention also provides methods for using the kit disclosed herein to procure and process autologous tissues for re-implantation in a patient.

The temporary storage and shipment solutions included in the kit may be bacteriostatic and/or bactericidal. The solutions may be a composition containing a disinfectant. The storage and shipment solutions may include a bacteriostatic agent and/or a bactericidal agent. The storage and shipment solutions may also include a preservation agent or plasticizer. The plasticizer may be glycerol. The plasticizer eliminates the need to ship and store the tissue at low temperature. As an example, the storage and shipment solutions may contain glycerol.

The device included in the kit allows the surgeon to drill one or more hole in the graft and to make screw threads. A syringe connector and tubing can be connected to the hole and used for flushing the treatment solution and rinsing solution through the tissue in the operating room and later at the processing facility. The microchip may contain the patient information and for documenting the treatment and processing conditions of the tissue.

The container included in the kit may have one or more openings or ports for liquids to enter and exit and an opening for placing the tissue into the container. The container may be deformable, nondeformable, or a combination thereof in which the container has a nondeformable exterior and a deformable interior. The container may be made of material that enables it to be deformable, or nondeformable or a combination thereof. The container may have an inlet opening and an outlet opening for rinsing solutions, treatment solutions, and storage solutions to enter and exit. The opening on the container for placing the tissue into or for removal of the tissue out of the container may be closed with a zipper or with a clamp. The process of cleaning, disinfecting, treating, storing, and/or shipping of the graft may all be performed in one container. The container may be a bag or may contain a bag with the features described above for the container.

In some aspects of the present invention, a collected tissue may be stored and processed in a processing container. In certain aspects, the processing container comprises at least one fluid (e.g., liquid or gas) inlet and one fluid outlet. The processing container may be large enough to contain a collected tissue and a treatment or processing composition. In some aspects of the present invention, the processing container is made of a material that does not react with the treatment composition(s) and/or processing composition(s), and can withstand centrifugation, and/or application of a vacuum. In certain aspects, the processing container remains undamaged, when its contents (i.e., bone tissue and a treatment solution, among others) are subjected to ultrasonication, cavitation, and/or high pressure air bubbles. In some aspects of the present invention, the processing container is deformable (i.e., a plastic bag, among others). In certain aspects of the present invention, a deformable processing container may adhere to the surfaces of the collected tissue during processing (i.e., when drawing a cleaning solution through the tissue using a vacuum) improving fluid penetration of the collected tissue.

In some aspects of the present invention, an autologous tissue collection kit may further include a tool for creating an instrument insertion site in a tissue. Certain autologous tissue collection kits of the present invention may further include a surgical instrument for re-implanting an autograft. In certain aspects of the present invention, the tool for creating an instrument insertion site in an autograft and the surgical instrument for re-implanting an autograft are the same. In some aspects of the present invention, the tool is used to create a threaded hole that is used as an instrument insertion site in a tissue.

Some autologous tissue collection kits of the present invention may include a treatment (or pre-treatment) composition for treating the tissue prior to processing, and the treatment composition may include at least one of a decontaminating agent (such as a bactericidal agent), a bacteriostatic agent, an enzyme, and a surfactant. The treatment composition may include glycerol or another plasticizer in certain aspects of the present invention. The treatment composition may include a decontaminating agent and a plasticizer in some aspects of the present invention.

A shipping container of certain autologous tissue collection kits of the present invention may include a compartment for holding patient records, a compartment for holding the sealable tissue container, and a compartment for holding at a treatment (or pretreatment) composition, a microchip, or a combination thereof. In some aspects of the present invention, the compartment for holding a sealable tissue container in a shipping container may be temperature controlled. Certain shipping containers used in the present invention may include labeling that indicates that the container holds biohazardous and/or human tissue. A shipping container may contain a donor identification, a patient's medical record number, name of a surgical facility where re-implantation of an autograft will take place, a record of the number of pieces of autograft tissue in the shipping container, and storage requirements, in some aspects of the present invention.

Certain aspects of the present invention are directed to an autologous bone graft for re-implantation into a recipient including a piece of bone that is autologous to the recipient, wherein the piece of bone includes an instrument insertion site that is capable of securely coupling to (1) a surgical placement instrument and (2) at least one of a solution injector and a solution evacuator. In some autologous bone grafts of the present invention, the instrument insertion site may be threaded. In some aspects of the present invention, the solution injector may be a syringe and the instrument insertion site acts as a syringe connection port. In certain aspects, the solution injector may be a pump that pumps a solution into an autologous bone graft through the instrument insertion site. Alternatively, a solution evacuator may be a pump that pumps (evacuates) a solution out of an autologous bone graft through the instrument insertion site. A solution that is injected or evacuated from an autograft may be a processing/treatment solution, a storage solution, or a rinse solution, among others, in some aspects of the present invention.

Certain autologous bone grafts of the present invention are prepared by a cleaning and/or processing method known in the art (see discussion above). In some aspects of the present invention, an autologous bone graft is prepared by a processing method including at least one cleaning step and at least one rinsing step. In certain aspects, a tissue that was collected from the patient may be processed using proprietary Allowash® technology of LifeNet Health, Virginia Beach, Va. in preparing an autologous bone graft of the present invention. In certain aspects of the present invention, an autologous bone graft is prepared by a processing method that includes at least one of perforating the bone graft, demineralizing the bone graft, applying a bioactive factor to the bone graft, and seeding the bone graft with viable cells. In certain aspects of the present invention, an autologous bone graft further includes at least one of an allograft tissue, a synthetic implant material, and a biocompatible adhesive (as discussed above) that may aid in at least one of wound healing, union of the graft with tissue at the implant site, and keeping the graft in place until union of tissues occurs.

Some autologous bone grafts of the present invention may be sterile. Certain autologous bone grafts of the present invention may be prepared from a tissue that had previously been contaminated with a bacterium, a single-celled eukaryote, or a virus. Some aspects of the present invention are directed to a packaged autologous bone graft having a sterility assurance level of at least about $10^{-6}$. In certain aspects of the present invention, a packaged autograft may be marked with an expiration date. An autograft may be packaged in a double peel pack pouch in some aspects of the present invention, and in certain aspects the double peel pack pouch may be validated to maintain integrity for at least 5 years.

The present invention may be used to pre-treat and process organs, as well as tissues, surgically removed from a patient. The organs after pre-treatment at the surgical facility may be packaged for shipping to a processing facility. After processing, the organs may be may be stored at the processing facility or packaged for shipping to the processing facility for re-implantation.

In some aspects of the invention, the tissue may be removed from a subject. The subject may be a patient. The patient may be an animal. The animal may be a mammal. The mammal may be a human, a cow, a pig, a goat, a dog, a horse, or a sheep.

Without further description, it is believed that one of ordinary skill in the art can, using the preceding description and the following illustrative examples, make and utilize the claimed invention. The following working examples therefore, specifically point out embodiments of the present invention, and are not to be construed as limiting in any way the remainder of the disclosure. All articles, publications, patents and documents referred to throughout this application are hereby incorporated by reference in their entirety.

EXAMPLES

Example 1

Figure 1B:
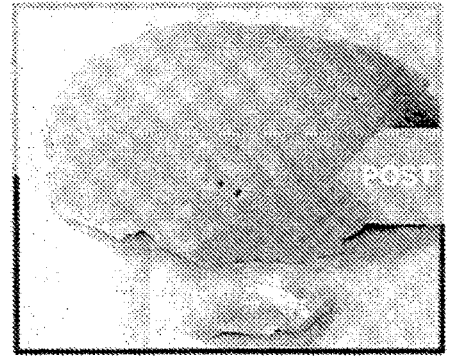
FIG. 1B is a picture of the bone flap of Example 1 after processing.

A right decompressive craniectomy was performed on a 43-year-old patient after a motor vehicle collision. The bone flap removed during the craniectomy was stored in a freezer at −80° C. On the 70th day after the injury, after the patient had recovered, surgeons performed a cranioplasty, using the stored bone flap to close the defect from the previous craniectomy. A week later, the patient presented with clinical symptoms of infection, including running a high fever. The cranial bone flap was removed, the patient was treated for the infection, and the bone flap was sent to LifeNet Health for processing. The bone flap was swabbed for contaminants during surgery and prior to processing at LifeNet Health, and *Enterobacter cloacae* were cultured from the swabs. (Swab cultures were tested for contaminating agents using both thioglycolate and trypticase soy broth media in a two-temperature/14-day culture protocol.) The bone flap was then cleaned and disinfected using processes that included LifeNet Health's proprietary Allowash® technology. Following processing, swab cultures taken from the bone flap were negative. Subsequently, the bone flap was treated with a controlled, low dose (i.e., 18 kGy to 58 kGy minimum absorbed dose) of gamma irradiation at low temperatures (i.e., −20° C. to −50° C.). The cleaned and irradiated bone flap was re-implanted in the patient after three months. There has been no recurrence of infection at the defect site, since the bone flap was re-implanted. Pictures of the bone flap before and after processing at LifeNet Health are shown in FIGS. 1A and 1B, respectively.

Example 2

Figure 2A:
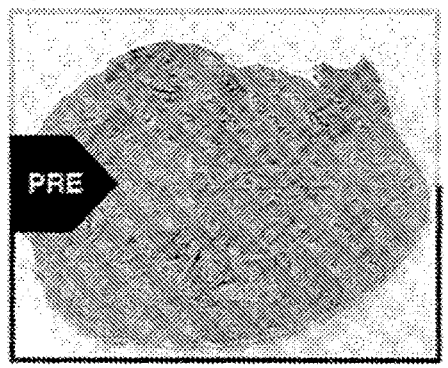
FIGS. 2A and B.
Figure 2B:
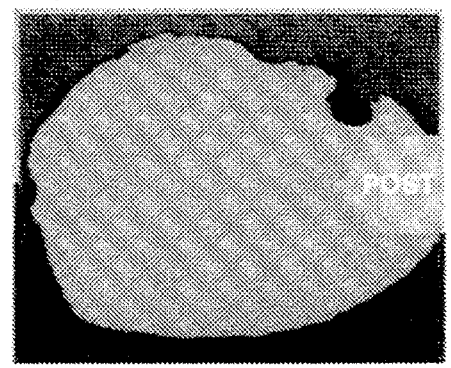
FIG. 2B is a picture of the bone flap of Example 2 after processing.

A left decompressive craniectomy was performed on a 20-year-old patient after trauma at Hospital A. The bone flap removed during the craniectomy was stored in a freezer at −80° C. Following his recovery, the patient was transferred to Hospital B for cranioplasty. The bone flap was transported to Hospital B on dry ice, but arrived at room temperature, and it was deemed unsafe for re-implantation. Hospital B stored the bone flap in its freezer at −80° C., until it could be sent to LifeNet Health for processing. At LifeNet Health, the bone flap was swabbed for contaminants, and *Staphylococcus epidermis* was cultured from the swabs. (Swab cultures were tested for contaminating agents using both thioglycolate and trypticase soy broth media in a two-temperature/14-day culture protocol.) The bone flap was then cleaned and disinfected using processes that included LifeNet Health's Allowash® technology. Following processing, swab cultures taken from the bone flap were negative. Subsequently, the bone flap was treated with a controlled, low dose (i.e., 18 kGy to 58 kGy minimum absorbed dose) of gamma irradiation at low temperatures (i.e., −20° C. to −50° C.). The cleaned and irradiated bone flap was re-implanted in the patient seven months later. There has been no recurrence of infection at the defect site, since the bone flap was re-implanted. Pictures of the bone flap before and after processing at LifeNet Health are shown in FIGS. 2A and 2B, respectively.

Example 3

Figure 3A:
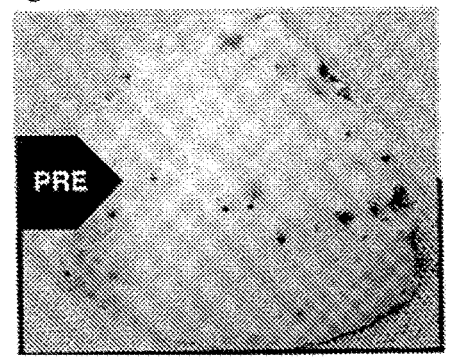
FIGS. 3A and B.
Figure 3B:
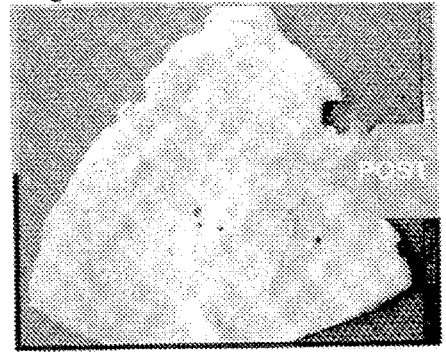
FIG. 3B is a picture of the bone flap of Example 3 after processing.

A craniectomy was performed during excision of a tumor in an 11-year-old, immune-compromised patient. The patient was immune-compromised due to tumor therapy. The bone flap was sent to LifeNet Health for processing. The bone flap was swabbed for contaminants, and *Staphylococcus aureus* and *Streptococcus viridans* were cultured from the swabs. (Swab cultures were tested for contaminating agents using both thioglycolate and trypticase soy broth media in a two-temperature/14-day culture protocol.) The bone flap was then cleaned and disinfected using processes that included LifeNet Health's Allowash® technology. Following processing, swab cultures taken from the bone flap were negative. Subsequently, the bone flap was treated with a controlled, low dose (i.e., 18 kGy to 58 kGy minimum absorbed dose) of gamma irradiation at low temperatures (i.e., −20° C. to −50° C.). The cleaned and irradiated bone flap was re-implanted in the patient six weeks later. There have been no complications reported, since the bone flap was re-implanted. Pictures of the bone flap before and after processing at LifeNet Health are shown in FIGS. 3A and 3B, respectively.

The invention claimed is:

1. A method of preparing a clean, disinfected autologous tissue implant for implantation, the method comprising
   a) pre-treating an autologous tissue surgically removed and collected from a patient,
   b) shipping the pre-treated autologous tissue to a tissue processing facility,
   c) receiving at the tissue processing facility the pre-treated autologous tissue that has been removed from the patient,
   d) processing the pre-treated autologous tissue to clean and disinfect the tissue, wherein the processing comprises treating the tissue with a detergent and a plasticizer,
   e) storing the processed autologous tissue at an external storage facility, and
   f) providing the clean, disinfected autologous tissue to a surgical facility for re-implantation into the patient.

2. The method of claim 1, wherein the autologous tissue comprises bone, tendon or ligament.

3. The method of claim 2, wherein the autologous tissue is a cranial bone flap.

4. The method of claim 2, wherein the processing comprises debridement.

5. The method of claim 2, wherein the processing comprises creating an instrument insertion site in the autologous tissue.

6. The method of claim 1, wherein the pre-treating comprises treating the collected autologous tissue with an antibiotic solution, a bactericidal solution, a virucidal, a glycerol-containing solution, water, saline or a combination thereof.

7. The method of claim 1, wherein the processing comprises exposing the autologous tissue to at least one bioactive factor.

8. The method of claim 1, wherein the autologous tissue is sterilized using irradiation after processing.

9. The method of claim 1, further comprising storing the processed autologous tissue in a storage solution.

10. The method claim 9, wherein the autologous tissue is irradiated while in the storage solution.

11. The method of claim 1, further comprising seeding cells onto the autologous tissue.

12. The method of claim 1, wherein the autologous tissue is a bone flap.

13. A method of preparing a clean, disinfected autologous tissue implant for implantation, the method comprising
 a) pre-treating autologous tissue surgically removed and collected from a patient,
 b) shipping the pre-treated autologous tissue to a tissue processing facility,
 c) receiving at the autologous tissue processing facility the pre-treated tissue that has been removed from the patient,
 d) processing the pre-treated tissue to clean and disinfect the autologous tissue, wherein the processing comprises treating the autologous tissue with a detergent,
 e) seeding cells onto the autologous tissue,
 f) storing the processed autologous tissue at an external storage facility, and
 g) providing the clean, disinfected autologous tissue to a surgical facility for re-implantation into the patient.

14. The method of claim 13, wherein the autologous tissue comprises bone, tendon or ligament.

15. The method of claim 14, wherein the autologous tissue is a cranial bone flap.

16. The method of claim 14, wherein the processing comprises debridement.

17. The method of claim 14, wherein the processing comprises creating an instrument insertion site in the autologous tissue.

18. The method of claim 13, wherein the pre-treating comprises treating the collected autologous tissue with an antibiotic solution, a bactericidal solution, a virucidal, a glycerol-containing solution, water, saline or a combination thereof.

19. The method of claim 13, wherein the processing comprises treating the autologous tissue with a plasticizer.

20. The method of claim 13, wherein the processing comprises exposing the autologous tissue to at least one bioactive factor.

21. The method of claim 13, wherein the autologous tissue is sterilized using irradiation after processing.

22. The method of claim 13, further comprising storing the processed autologous tissue in a storage solution.

23. The method claim 22, wherein the autologous tissue is irradiated while in the storage solution.

24. The method of claim 13, wherein the autologous tissue is a bone flap.

25. A method of preparing a clean, disinfected autologous tissue implant for implantation, the method comprising
 a) pre-treating autologous tissue surgically removed and collected from a patient,
 b) shipping the pre-treated autologous tissue to a tissue processing facility,
 c) receiving at the tissue processing facility the pre-treated autologous tissue that has been removed from the patient,
 d) processing the pre-treated autologous tissue to clean and disinfect the autologous tissue, wherein the processing comprises treating the autologous tissue with a detergent,
 e) storing the processed autologous tissue at an external storage facility, and
 f) providing the clean, disinfected autologous tissue to a surgical facility for re-implantation into the patient,
 wherein the autologous tissue is a bone flap.

26. The method of claim 25, wherein the autologous tissue is a cranial bone flap.

27. The method of claim 25, wherein the pre-treating comprises treating the collected autologous tissue with an antibiotic solution, a bactericidal solution, a virucidal, a glycerol-containing solution, water, saline or a combination thereof.

28. The method of claim 25, wherein the processing comprises debridement.

29. The method of claim 25, wherein the processing comprises treating the autologous tissue with a plasticizer.

30. The method of claim 25, wherein the processing comprises creating an instrument insertion site in the autologous tissue.

31. The method of claim 25, wherein the processing comprises exposing the autologous tissue to at least one bioactive factor.

32. The method of claim 25, wherein the autologous tissue is sterilized using irradiation after processing.

33. The method of claim 25, further comprising storing the processed autologous tissue in a storage solution.

34. The method claim 33, wherein the autologous tissue is irradiated while in the storage solution.

35. The method of claim 25, further comprising seeding cells onto the autologous tissue.

* * * * *